United States Patent [19]

Charvet-Faury et al.

[11] Patent Number: 5,708,000
[45] Date of Patent: Jan. 13, 1998

[54] N4-SUBSTITUTED CYTOSINYL 1,3-OXATHIOLANE NUCLEOSIDE ANALOGUES, AND THEIR ANTIVIRAL ACTIVITY

[75] Inventors: Anne Sophie Charvet-Faury, Marseille; Michel Camplo; Jean Louis Kraus, both of Ile-sur-Sorgues, all of France

[73] Assignee: Laboratoire Laphal, France

[21] Appl. No.: 586,892

[22] PCT Filed: May 24, 1995

[86] PCT No.: PCT/FR95/00683

§ 371 Date: Jan. 19, 1996

§ 102(e) Date: Jan. 19, 1996

[87] PCT Pub. No.: WO95/32200

PCT Pub. Date: Nov. 30, 1995

[30] Foreign Application Priority Data

May 24, 1994 [FR] France ................... 94 06262

[51] Int. Cl.$^6$ .............. A61K 31/505; C07D 239/02
[52] U.S. Cl. ............ 514/274; 544/311; 544/312; 536/28.5; 536/28.51; 536/28.52; 514/49
[58] Field of Search ............ 536/27.11, 28.5, 536/28.51, 28.52; 544/312, 311; 514/274

[56] References Cited

FOREIGN PATENT DOCUMENTS 0515144 11/1992 European Pat. Off. .
9208717 5/1992 WIPO .
9532200 11/1995 WIPO .

OTHER PUBLICATIONS

Camplo et al., "Synthesis and Antiviral of N-4'-dihydropyridinyl and dihydroquinolinylcarbonyl-2-hydroxymethyl-5-[cytosin-1'-yl]-1,3-oxathiolane Derivatives Against Human Immunodeficiency Virus and Duck Hepatitis B Virus," *European J. Medicinal Chem.*, 31, 539–546 (1996).

Storer et al., "The Resolution and Absolute Stereochemistry of the Enantiomers of cis-1-[2-(hydroxymethyl)-1,3-oxathiolan-5-yl] cytosin," *Nucleosides and Nucleotides*, 12(2), 225–236 (1993); *Chem. Abstr.*, 119(5), p. 999, Abstr. No. 49821h (Aug. 2, 1993); only Abstract supplied.

Camplo et al., "Synthesis and Antiviral Activity of a Potential Prodrug: $N^4$-Retinoyl-3'-thia-2',3'-dideoxycytidine," *Medicinal Chem. Res.*, 3(2), 87–95 (1993); *Chem. Abstr.*, 119(23), p. 16, Abstr. No. 240935c (Dec. 6, 1993); only Abstract supplied.

Camplo et al., "Synthesis and Comparative Anti-HIV Activities of New Acetylated 2',3'-Dideoxy-3'-thiacytidine Analogs," *European J. Medicinal Chem.*, 29(5), 357–362 (1994); *Chem. Abstr.*, 121(21), p.53, Abstr. No. 245179k (Nov. 21, 1994); only Abstract supplied.

Charvet-Faury et al., "Inhibition of Human Immunodeficiency Virus Type 1 Replication by Phosphonoformate-and Phosphonoacetate-2',3'-Dideoxy-3'-thiacytidine Conjugates," *J. Medicinal Chem*, 37(14), 2216–2223 (1994); *Chem. Abstr.*, 121(19), p. 1143, Abstr. No. 231238s (Nov. 7, 1994); only Abstract supplied.

Kim et al., "Potent Anti-HIV and Anti-HBV Activities of (−)-L-β-Dioxolane-C and (+)-L-β-Dioxolane-T and Their Asymmetric Syntheses," *Tetrahedron Letters*, 33(46), 6899–6902 (1992).

*Primary Examiner*—John Kight
*Assistant Examiner*—L. Eric Crane
*Attorney, Agent, or Firm*—Bierman, Muserlian & Lucas

[57] ABSTRACT

The present invention pertains to the field of organic chemistry, and particularly therapeutic chemistry. The invention provides cis-form 5-(cytosinyl-1) 1,3-oxathiolanes of general formula (I), wherein R is an acyl or aralkoyl radical, derivatized from a nitrogen monocyclic or bicyclic heterocycle, and the hydroxymethyl group in position 2 is in cis position in relation to the plane defined by positions 2 and 5. The compounds of general formula (I) are useful as active ingredients in pharmaceutical compositions, particularly with antiviral activity.

15 Claims, No Drawings

N4-SUBSTITUTED CYTOSINYL 1,3-OXATHIOLANE NUCLEOSIDE ANALOGUES, AND THEIR ANTIVIRAL ACTIVITY This invention relates to the field of organic chemistry and more precisely to that of medicinal chemistry.

More particularly it has as a subject matter 2',3'-didesoxynucleosides substituted in position 2 with an oxathiolane ring.

Specifically this invention has as a subject matter the 5-(citosinyl)1,3-oxathiolanes of cis configuration (2R-5S) or (2S-5R) having the general formula:

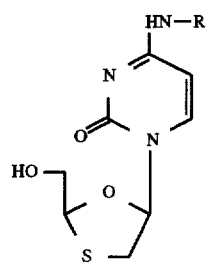

which may be represented with one out the two spatial representations:

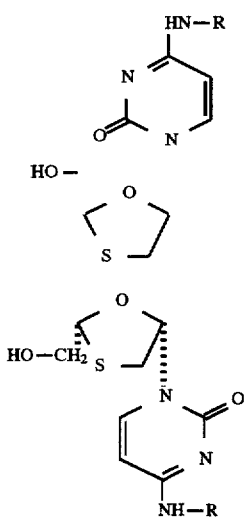

wherein R is an acyl radical or an aralkyl radical, derived from a monocyclic or bicyclic nitrogenous heteroring and the hydroxymethyl group in position 2 is in cis position relating to the plane determined by the two positions 2 and 5.

Among the various definitions taken by the substituent R, it may be differentiated a) the nicotinic derivatives where the heteroring is a pyridinic structure and the acyl moiety is in position 2, 3 or 4, having the formula Ia

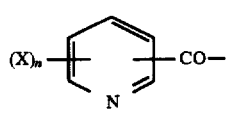

wherein X is a hydrogen, a halogen atom, a nitro group, a lower alkoxy or a trifluoromethyl radical and n is a integer from 1 to 3 b) the dihydropyridic derivatives wherein the heteroring is a 1,4-dihydropyridinic structure and the acyl radical is in position 2, 3 or 4, having the formula Ib

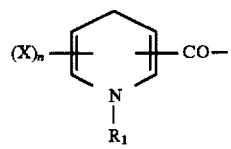

wherein $R_1$ is an alkyl radical having from 1 to 10 carbon atoms and X and n are defined as previously c) the quaternized nicotinic derivatives wherein the nitrogen atom bears an alkyl substituent and the acyl radical is in position 2, 3, or 4, having the general formula Ic

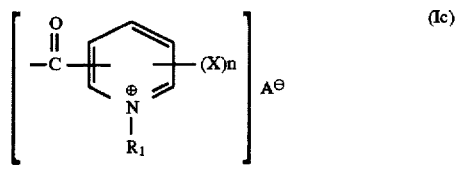

wherein A is an inorganic or organic anion and $R_1$, X and n are defined as previously d) the quinoleinic derivatives wherein the heteroring is a bicyclic structure, having the general formula Id

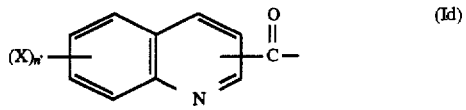

wherein the carbonyl radical may be in position 2, 3, or 4, X represents a hydrogen, a halogen, a trifluoromethyl radical, a lower alkoxy or a nitro group and n' represents an integer from 1 to 6.

e) the dihydroquinoleines of general formula Ie

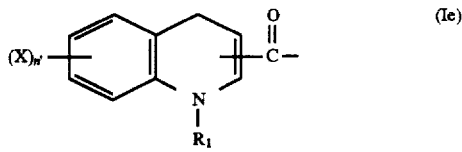

wherein $R_1$ and X are defined as previously and n' is an integer from 1 to 6.

f) the quaternized quinoleins of general formula If

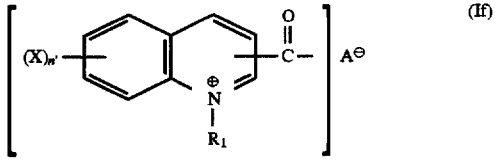

wherein $R_1$, X and n' are defined as previously the acyl radical is present in position 2, 3, or 4, and A is an inorganic or organic anion g) the (dihydropyridyl) alkyl derivatives of general formula Ig

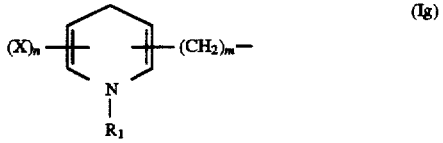

wherein $R_1$, X and n are defined as previously and m is an integer from 1 to 6 as well as the acid addition salts thereof with a mineral or organic acid.

The compounds of formula I may be resolved in their optically-active isomers. It may thus be obtained the isomer (+) and the isomer (–).

The retroviral infections are the cause of severe infections, particularly that of acquired immunodeficiency syndrom (AIDS) which is a vital infection often lethal and to a lesser degree hepatitis. Several compounds of nucleosidic or hetero-nucleosidic types are presently clinically utilized for the treatment of these retroviral infections. The former ones are the derivatives of AZT (3'-azido-2',3'-didesoxythymidine) (Proc. Natl. Acad. Sci. 82, 7096–7100, 1985), ddC (2',3'-didesoxycytidine)(Proc. Natl. Acad. Sci. 86, 1911–15, 1986), d4T (2',3'-didehydro-3'-desoxythymidine) (Biochem. Biophys. Res. Comm. 142, 128–34, 1987), ddI (2',3'-didesoxyinosine) (Antiviral. Chem Chemother 2, 221, 1991), BCH-189 or 3TC (2',3'-dideoxy 3'-thiacytidine) disclosed in the european patent application 90301335.7 and the followings. The limited number of the anti-retroviral compounds available to the practioner ant the limited efficacy suggested the search of new compounds, the therapeutic virtues of which would be increased and the side-effects will be decreased Some derivatives of2-[(1-hydroxymethyl) 1,3-oxathiolan-5yl] cytosin and namely the esters of the hydroxymethyl function (european patent application 0,382, 526) or the halogenated derivatives in position 5' of the pyrimidine ring are already known (R. F. SCHINAZI et al. Antimicrob Agents and Chemotherapy 36(1992) 2423–2431).

The compounds of this invention possess the ability to inhibit the replication of human retroviruses, particularly VIH and hepatites B (HBV). The compounds derived from BCH-189 or TC-3, include in their structure a 1,4-dihydro 1-methyl 3-quinoleylcarbonyl grouping bound to the exocyclic amino group of cytidine. This particular structural entity gave in experimental pharmacology, the ability to increase and to facilitate the permeation of the hematoencephalic barrier (Pharmacol. Ther 19, 337–396, 1983—Methods Enzymol 112, 381–396, 1985—Drug. Des. Del. 1, 51–64, (1986)—J Med. Chem 31, 244–249, 1988—J. Med. Chem. 32, 1782–1788, 1989—J. Med. Chem. 32, 1774–1781, 1989).

The chemical synthesis of these compounds has been carried out using classical experimental protocols. The performance of these novel heteronucleosides requires as starting material, the compound 2',3'-didesoxy 3'-thiacytidine for which several methods of synthesis have been reported in the chemical litterature (J. Org. Chem. 56, 6503, 1991—J. Org. Chem. 57, 2217, 1992—Tet. Lett. 33, 4625, 1992—Nucleosides and Nucleotides 12, 225, 1993). Starting from this derivative, the synthesis of the compounds which are the subject matter of this invention, and that of the intermediate compounds, which are related thereto, are also described in this application.

This invention also relates to a process for producing the compounds of general formula I which consists in that a 5-(cytosinyl-1) 1,3-oxathiolane cis is submitted to the action of a functional derivative of a carboxylic acid of formula ROH wherein R is an acyl moiety derived from an aromatic or dihydroaromatic, mono- or bicyclic nitrogenous heteroring or to the action of an aralkylated active derivative of formula R'Z wherein R' is an aralkyl radical deriving from an aromatic or dihydroaromatic, mono- or bicyclic nitrogenous heteroring and Z is an easily split, labile radical.

In a more precise manner, the functional derivative of acid ROH is an halogenide, an anhydride, a mixed anhydride obtained from a carbodiimide or a reactive ester such a phenolester.

In the case of an arylakylated derivative, Z is a halogen atom or an alkyl- or arylsulphonyl radical.

This invention has also as a subject matter the pharmaceutical compositions with anti-viral action characterized in that they include as an active ingredient at least one compound of general formula I, or an addition salt thereof with a mineral or organic acid, in admixture or in association with an inert, non toxic, pharmaceutically-compatible carrier or vehicle, notably suitable for the topic or systemic use.

In these compositions the contents in active ingredient of general formula I ranges from 0.1 mg to 100 mg per unit dosage as a function of the way of administration.

EXAMPLE I

Isomers of cis 2-(diphenyltertbutylsilyloxymethyl)-5 [$N^4$-(3" -pyridinylcarbonyl) cytosinl '-yl]-1,3-oxathiolane 1

At room temperature under nitrogen stream, they are added to a mixture of dichloromethane (7 ml) and dimethyl formamide (2 ml) leq. of nicotinic acid (27 mg. 0.21 mmol). 1.1 eq. of BOP (93 mg. 0.23 mmol). 1.1 eq of HOBT (31 mg. 0.23 mmol). 1 eq of 5'-tertbutyldiphenylsilyl-2',3'-didesoxy-3'-thiacytidin (39 mg. 0.23 mmol) and 4 eq. of DIEA (146 µl. 0.84 mmol). The mixture is stirred for a night at room temperature, washed with a 5% citric acid solution (10 ml) then with an 5 % aqueous solution of sodium bicarbonate (10 ml). The resulting mixture is extracted with ethyl acetate (3×10 ml), dried on $SO_4$ $Na_2$, and evaporated The residue is purified on silica gel plate 48 mg of pure compound are obtained.

[$^1$H]NMR δ ($CDCl_3$)=1.1 (s,9H.tBu). 3.1–3.6 (m,2H, $CH_2$-O): 3.7–4.2 (m,2H,$C_4H_2$); 5.25 (t, 1H,$C_5$-H); 3.1–3.6 (m,2H,$CH_2$-O), 5.5 (d, 1H,$C_5$'-H): 6.35 (q,1H,$C_2$-H); 7.4–7.8 (m. 1H,aromatique); 8.0 (d,1H,$C_6$'-H): 8.3 (d,1H, nicotinyl); 8.8 (d,1H,nicotinyl); 8.8 (d,1H,nicotinyl); 9.1 (d,1H,nicotinyl).

EXAMPLE II

Isomers of Cis 2-(hydroxymethyl)-5 [$N^4$-(3"-pyridinylcarbonyl)cytosin-1'-yl]-1,3-oxathiolan 2

The compound 1 (25 mg, 0.05 mmol) is dissolved in 3 ml anhydrous tetrahydrofuran. To this solution 3 eq (135 µl, 0.15 mmol) of tetrabutylammonium fluoride are added. The solution is mixed at room temperature for 3 hours. After evaporation of the solvent, the resulting product is chromatographied on preparative silica plates (eluent : toluene/ $CH_3OH$ 15%). 13 mg of desired compound are obtained.

[$^1$H] NMR δ ($CDCl_3$)=3.1–3.6 (m,2H,$CH_2$-O), 3.7–4.2 (m,2H,$C_4H_2$): 5.25 (t,1H,$C_5$-H), 5.5 (d.H.$C_5$'-H), 6.35 (q.1H.$C_2$-H). 7.4–7.8 (m,1H,aromatique), 8.0 (d, 1H,$C_6$-H), 8.3 (d,1H,nicotinyl) 8.8(d.1H,nicotinyl) 9 1 (s. 1H,nicotinyl).

EXAMPLE III

Isomers of Cis 2-(tertbutyl-diphenyl-silyloxymethyl)-5-[$N^4$-(3"-(tosyl) cytosin-1'-yl]-1,3-oxathiolane 4

To a solution of compound 5 (56 mg, 0.12 mmol) in pyridine (3 ml) they are added at 60° C. under nitrogen atmospher, 2 eq of p.toluene sulphonic acid chloride (46 mg, 0.24 mmol). After 20 hours stirring at room temperature, the mixture is evaporated off, washed with a 5% citric acid solution (10 ml) then extracted with ethyl acetate (3×10 ml).

The united organic phases are dried on $Na_2SO_4$ and evaporated. 48 mg of the desired compound are isolated.

[$^1$H]NMR:(CDCl$_3$)=1.1 (s,9H,tbu): 2.45 (s,3H,CH$_3$ tosyl): 3.15–3.55 (m, 2H, C$_2$-CH$_2$-0); 3.85–4.2 (m,2H, C$_4$H$_2$): 5.25 (t,1H,C$_5$-H) 6 3 (t,1H,C$_2$-H); 7.3–7.7 (m, 14H, ArH); 8.05 (d,1H,C$_6$-H);

EXAMPLE IV

Isomers of cis 2-(diphenyltertbutyl silyloxymethyl)-5-[N4(3"-pyridinylcarbonyl)cytosin-1'-yl] 1,3-oxathiolane 3

To a solution of derivative 4 (47 mg, 0.075 mmol) in lutidine (2 ml) under nitrogen atmospher at 90° C. they are added 6 eq (46 µl 0.45 mmol) of pyridinylmethylamine. Heating is kept for 48 hours under stirring After cooling the mixture is evaporated, washed with a 5% citric acid solution (10 ml) then extracted with ethyl acetate (3×10 ml) and dried on Na$_2$S O$_4$. After evaporation the residue is purifyied by chromatography on silica gel plate (eluant EtOAC/MeOH, 10/1)

EXAMPLE V

Isomers of cis 2(tertbutyldiphenylsilyloxymethyl)-5-(cytosin- 1'-yl)-1,3-oxathiolane 5

A solution of 2',3'-didesoxy 3'-thiacytidine (105 mg, 0,45 mmol) in pyridine (6 ml) is treated under nitrogen atmospher with diphenyltertbutylsilyl chloride (140 µl, 0,5 mmol). The reaction mixture is stirred for 24 hours at room temperature. After concentration under vaccuum, they are added 30 ml water and it is extracted with ethyl acetate (3×20 ml). The united organic phases are then dried on $Na_2SO_4$ and concentrated to dryness to give the compound 5 (210 mg, quantitative yield) in the form of a white solid.

Rf(AcOEt/MeOH2/1)=0,62

[$^1$H]NMR(CDCl$_3$) δ: 1,1, (s,9H,tbu); 3,1–3,6(m,2H,C$_2$-CH$_2$-O): 3,7–4,2 (m,2H,c$_4$-H$_2$); 5,25 (t,1H,C$_5$-H); 5.5 (d,H, C$_5$-H) ;6,35 (q,1H,C$_2$-H) 7,4–7,8 (m,10H,2Ph); 8,0 (d,1H, C$_6$-H)

EXAMPLE VI

Isomers of cis 2-(hydroxymethyl)-5-[N4-(1"-methyl-3"-pyridinylcarbonyl)cytosin -1'-yl]-1,3-oxathiolane 6 as the iodide.

Under nitrogen atmospher to 1 eq. (46 mg, 0,14 mmol) of compound 2 dissolved in 4 ml anhydrous acetonitrile, they are added 9 eq. (1,25 mmol, 77 µl) methyl iodide. The resulting solution is heated to 50° C. for 48 hours. After evaporation of the solvants, the residue is purified by flash chromatography with as eluant BuOH/H$_2$O acetic acid (5:2, 5:2,5). A yellow solid is obtained (55 mg).

[$^1$H]NMR: (DMSO d$_6$) δ=3.25 (t,2H,CH$_2$-4); 3.90 (dd, 2h,C$_2$-CH$_2$); 4,45 (s,3H,N$^+$-CH$_3$); 5.25 (t,1H,CH-5); 6.30 (t,1H,CH-2): 6.92 (d,1H,CH-6'); 7.30 (d,1H,nicotinyl); 7.85 (d,1H,nicotinyl); 8.05 (d,1H,CH-5'); 8.20 (d,1H,nicotinyl); 7.85 (d,1H,nicotinyl); 9.01 (d,1H,nicotinyl).

Mass spectrum (FAB$^+$)349(M- 1)$^+$

EXAMPLE VII

Isomers of cis 2-(hydroxymethyl)-5-[N$^+$-(1"-methyl)-1",4"-dihydro-3"-pyridinyl carbonyl) cytosin-1'-yl]-1,3-oxathiolane 7

In 3 ml of degased solution of methanol containing 10% water, they are dissolved 30 mg (0,06 nM)of compound 6.

To this solution they are added 15 mg of sodium bicarbonate and 60 mg sodium dithionite. The reaction mixture is stirred under nitrogen tbr 3 hours. The solution becomes orange. The solvent is evaporated then the salts are resuspended in a minimal amount of methanol. One filters. The filtrate is purified by preparative chromatography on thin layer (1 mm) (eluant : Toluene/methanol 1.1) to give 6 mg of a yellow white solid Mass spectrum (FAB')349 (M-1)

EXAMPLE VIII

Isomers of cis 2-hydroxymethyl 5-[N$^4$-3"-quinolinylcarbonyl) cytosin-1'-yl] 1,3-oxathiolane 8

To 2 ml anhydrous dimethylformamide they are added 74.4 mg (0.43 mmol) quinolinyl -3-carboxylic acid then 96 mg (0.47 mmol) 1,3-dicyclohexyl carbodiimide and 63,4 mg (0.47 mmol) hydroxybenzotriazole hydrate. The mixture is stirred for 1 hour at room temperature under nitrogen. A white precipitate of dicyclohexylurea appears and 100 mg (0,43 mmol) 2,3'-didesoxy 3'-thiacytidine are then added. The mixture is stirred over night. Dimethyl formamide is thereafter evaporated under reduced pressure and the residue is hydrolysed with a saturated aqueous solution of NaCl (10 ml). The residue is extracted two times with ethyl acetate (2×10 ml). The organic phases are combined, dried on magnesium sulphate and filtered. The solvent is evaporated. The product is purified by (flash) chromatography (eluant : ethyl acetate/methanol 98:2) to give 78 mg of a white solid (0,2 mmole) i.e. a yield of 46,5%. MP=116°–118° C. IR=1656 cm$^{-1}$ (carbonyl of the amide function).

[$^1$H]NMR:(DMSO d$_6$) δ=11,75 (s,1H,NH);9,40 (d,1H, CH-2");9,15 (d,1H, CH-4"); 8.65 (d,1H,CH-5'); 8.20 (m,2H, CH-8" et -CH-5"); 8.0 (m,1H,CH-6"); 7.80 (m,1H,CH-7"): 7.45 (d,1H,CH-6'): 6.35 (t,1H,CH-2); 5.55 (t,1H,CH-5); 3,98 (t,2H,C$_2$-CH$_2$-4) [$^{13}$C]NMR : (DMSO d$_6$ ) δ=37.14 ((C-4): 61,95 (CH$_2$O-C2); 87,28 (C-2): 88,29 (C-5); 95,85 (C-5'); 122,21 (C-3"); 126.28 (C-6"); 127,71 (C-5"): 129,63 (C-10"): 129,87 (C-7"); 132,08 (C-8"); 137,65 (C-4"); 138, 89 (C-6'); 148,91 (C-9"); 149.29 (C-2"); 163,16 (C-2'); 164.51 (C-4')

Mass spectrum (Fab$^+$) 385 (M+1)$^+$, 769 (2M+1)$^+$

EXAMPLE IX

Isomers of cis 2-hydroxymethyl 5-[N$^4$-(1"-methyl 3"-quinolinyicarbonyl)cytosin-1'yl]-1,3-oxathiolane 9 as the iodide.

A solution of compound 8 (78 mg i.e. 0,20 mmol) in 4 ml acetonitrile is prepared. To this 112 µl (1.8 mmol) methyl iodide are added and the mixture is heated to 40° C. under nitrogen for 24 hours. The solvent is eliminated and the crude residue is then dissolved in the minimal amount of acetonitrile. It is a new precipitated by adding ether. An orange solid is thus obtained (60 mg i.e. a yield of 55%)

MP=156°–159° C.

[$^1$H] NMR (CD$_3$OD) δ=3.32 (t,2H CH$_2$-4), 3.99 (dd,2H,C$_2$-CH$_2$) 4 80 (s.3H $^+$N CH$_3$) 5 38 (t 1H CH-5) 6.0 (d.1H.CH-6') 6.33 (t.1H.CH-2) 8 13 (m 1H CH.7"). 8 39 (m 1H CH-6") 8 60 (m.2H.CH-8") 8.72 (d.1H.CH-5') 9.79 (d 1H CH-4"). 9 95 (d 1H CH-2")

Mass spectrum (Fab) 399 [M-1]. 799 [2(M-1)]

EXAMPLE X

Isomers of cis 2-hydroxymethyl 5-[N$^4$-(1"-methyl 1", 4"-dihydro 3"-quinolinylcarbonyl) cytosin-1'yl]-1,3-oxathiolane 10

To a solution of 30 mg (0,057 mmol) of compound 9 in 3 ml degased aqueous methanol (3 ml methanol containing 10% water), 15 mg of sodium bicarbonate and 60 mg sodium dithionite are added. The whole mixture is stirred for one hour under nitrogen. The solvent is evaporated and the crude residue is purified by preparative chromatography (eluent : ethyl acetate/methanol 1:1). Finally 10 mg of a vitreous yellow solid are obtained, i.e. a yield of 46%.

[$^1$H] NMR : (D$_2$O) δ=3.24 (m,3+2H.NCH$_3$+CH$_2$-4"); 3.48 (m,2H.CH$_2$-4); 3.93 (m,2H.C$_2$H$_2$); 5.29 (t,1H.CH-5); 6.96 (d.1H.CH-6'); 7.13 (m,2H.CH-6"+CH-7"); 7.27 (m,2H. CH-5"+CH-8"). 7.45 (d.1H.CH-2"); 8.23 (d.1H.CH-5')

Mass spectrum: (Fab$^-$) 399 (M-1)$^+$

EXAMPLE XI

Isomers of cis 2-hydroxymethyl-5-[N$^4$-(2-(a,a,a-trifluoro-m-toluidino)nicotinyl)-cytosin-1'yl]-1,3-oxathiolane 11

To a solution of 2',3'-didesoxy 3'-thiacytidine (50 mg, 0.2 mmol) in 5 ml anhydrous DMF they are added 1,1 eq. BOP (93 mg 0.23 mmol, 1 eq. niflumic acid (2-a,a,a-trifluoro-m-toluidino nicotinic add) and 4 eq. DIEA (146 µl, 0.84 mmol). The mixture is stirred overnight at room temperature, washed with a 5% citric acid solution (10 ml) then with a 5% aqueous solution of sodium bicarbonate (10 ml). The resulting mixture is extracted with ethyl acetate (3×10 ml) dried on sodium sulphate, then evaporated.

The residue is purified by chromatography on a column of silica gel (eluent : ethyl acetate/toluene 1:9). It is obtained a white solid (49 mg, yield: 48%).

TEST OF EVALUTATION OF THE ANTIVIRAL PROPERTIES

ANTI-HIV TESTS - Experimental protocol a) Generalities

Apparatus : an ultricentrifugal of Beckman type TL100 is used. Counting of the radio labelled particles is performed on a Hewlett Packard apparatus Tri Carb Model 1600. The syncitia are observed with an invert microscope Labovert.

Composition of the lysis buffer NTE:

| | |
|---|---|
| Trishydroxymethylaminomethane | 10 mM |
| ClNa | 100 mM |
| EDTA | 1 mM | b) Evaluation tests of the antiviral properties in cell cultures

The evaluation of the antiviral action is based on the study of cytopathogenic effect of HIV-1 Virus on the cell line MT4. The cell line MT4 has as an origin T cells isolated from a patient, transformed by the TLHV-I virus. The cytopathogenic effect of HIV-1 virus is shown by the formation of multinucleated giant cells called <<syncithia>> visible under the microscope. This effect of HIV-1 is observed 4 to 5 days after infection. It is followed with the death of cells.

The cytopathogenic effect is directly correlated to the infection of the cells by the virus, to its intracellular replication and to the expression of viral antigens by the cells. An inhibition of this effect thus corresponds to an inhibition of the multiplication of HIV-1 virus.

The MT4 cells are maintained at 3.10$^5$ cells/ml in a RPMI 1640 medium : 10% of decomplemented fetal calf serum for 30 mn at 56° C. (hormons, serum growth factors . . . ), 1% glutamine, 1% penicillin streptomycin and 2 µg/ml Polyren which promotes the viral adhesion to the cells.

The action of the treatment by the anti-viral agent is continuous. In fact this effect is present before during and after the viral infection. Successive dilutions are performed in the 10% fetal calf serum to be able to cultivate the MT4 cells for 8 days and to observe the formation of syncithias.

MT4 TEST

Before infection : 3×10$^6$ cells/100 µl are distributed in a microtiter plate with 96 wells and centrifugated for 3 min. at 2000 rpm (rounds per minute). The pellet is then pre-incubated for 1 hour at 37° C., with 100 µl of various concentrations of the anti-viral agent to be tested.

Infection : The infection is achieved in microwells while adding 100 TCIU (infection units) of HIV-1 virus (this titer of HIV-1 virus is determined as to induce the formation of syncithias in 4 or 5 days). The anti-viral agent is always present at the time of infection and dilution of the virus at 100 TCIU.

After infection : After incubation for 1 hour at 37° C., the MT4 cells are washed three times with RPMI 1640 medium and cultured on account of 3.10$^5$ cells per milliliter of each of the concentration of the compounds to be tested on plates of 24 wells. When passing at day D$_3$ the MT4 cells are diluted to ½. The concentration of the anti-viral agent is maintained. Each day occurrence of syncithia is observed under the microscope to detect any optional delay with respect to the controls HIV-1. At day D$_8$ the determination of reverse transcriptase is carried out. When the cells are not infected thus it is a protection by the tested anti-viral agent.

Determination of reverse transcriptase

Reverse transcriptase is a RNA dependant DNA polymerase. This enzyme allows the replication of retroviruses. Thank to it, the vital RNA transcribed into DNA, is incorporated in the cell genome. Provital DNA is transcribed by the cell enzymes into a viral RNA. For the determination of the reverse transcriptase activity, one concentrates 100 times 1 ml of supernatant of culture, by ultra centrifugation for 5 min at 95000 rpm. The pellet of virus obtained after ultra-centrifugation is resuspended into 10 µl of buffer NTE+ TRITON 0.1% (polyoxyethylene ether). The latter is used to lysate the virus and to release the reverse transcriptase. In vitro it is the reverse transcriptase activity which is evidenced. This enzyme uses a synthetic matrix poly A possessing a primer oligo dT having from 12 to 18 residues. The radio labelled substrate of this reaction is [$^3$H]dTTP (radio active thymidin triphosphate at 1 mCi/ml). The novelly formed tritiated macromolecules are precipitated by trichloroacetic acid and separated from free [$^3$H] TTP by filtration. The enzymatic activity of the reverse transcriptase is measured through the radioactivity incorporated in the complexes poly-rA/poly -dT. This radiolabelling is determined in a particle counter after addition of a scintillation liquid acting as an amplifyier.

ANTI-HBV TEST - EXPERIMENTAL PROTOCOL

Among the several methodologies used for evaluating the activity of compounds on Hepatitis B virus (HBV), the pattern of Hepatitis B virus of the duck (Duck HBV) has been utilized (J. Med. Virology (1990) 31 82–89 ; Viral Hepatitis and Liver disease (1988) 506–509 ; Hepatology (1989) 10 186–191). The material of culture to test <<in vitro>> the anti HBV activity of the compounds is made of duck hepatocytes infected by the duck Hepatitis B virus (DHBV) (Antimicrob. Agents Chemother. (1989) 33 336–339 ; J. Med. Virology 40,59–64 ; Antivir Res. (1993) 21, 155–171 ; Antimicrob. Agents Chemother. (1993) 37 1539–1542). Indeed the Hepatitis B virus of the duck is recognized as being very close to the human hepatitis B virus (Viral Hepatitis and Liver Disease (1988) 526–529. Antiviral Research (1987) 8189–199). Under standardized conditions (Virology (1989) 171 564–572) the cultures of duck hepatocytes allow the complete replication of DHBV. The antiviral activity of the tested compounds has been measured as a function of the amount of viral DNA produced during 10 days of culture of the infected hepatocytes.

Experimental Protocol

A young male duck 3 weeks old, affected by DHBV, is used for the production of hepatocytes. The duck is killed under anesthesia and the isolation of hepatocytes is carried out using the methodology of Guillouzou (Research in isolated and cultured hepatocytes, J. Libbey Eurotex Ltd / INSERM, 1986). The cells are cultured in the Leibowitz's medium and 5 µg/ml bovine insuline, $7 \times 10^{-5}$ mole cortisone hemisuccinate and 1.5% dimethylsulfoxide (DMSO) are added thereto. The density of the cells is $8 \times 10^6$ cells, they are sprayed in culture boxes of 100×20 mm. The tested compounds are added to the culture after the spread out of the cells. The medium is renewed every day, during 10 days. The production of viral DNA of the duck hepatitis B virus in the cells surpernatant is determined by means of hybridation method "Dot blot" according to Fourel and al. (Viral Hepatitis and Liver Disease, 1988, 506–509 ; Hepatology, 1989, 10, 186–191). Inhibition is expressed as a percentage of the DNA amount present on the supernatant of cells with regard to a culture infected by DHBV untreated with a nucleosidic derivative.

VIROLOGICAL RESULTS

HIV Tests

The compounds the synthesis of which has been described in this patent application and the related structures given in the previous prior art, have an affect on the inhibition of the replication of BRU HIV-1 virus (BRU beeing the vital strain experienced) in the case where the infected cells are of the type MT4.

In the table I they have been described the results of the tests. Column 1 provides the names of the most representative studied compounds and in column 2 they are reported the so-called $IC_{50}$ values (concentration of the component giving a 50% inhibition of the replication of HIV in the infected MT4 cells, measured at day D7 after infection). In observing and counting the number of formed syncitia in relation with that counted in the case of infected MT4 cells but untreated with antiviral compound, the value $IC_{50}$ is determined.

DBHV Tests

The most representative described compounds have been tested for their effect on the replication of the duck virus HBV (DHBV) along the protocol exposed in the experimental part of this document.

In the table II the results of the tests are described.

ABREVATIONS

AcOEt: ethyl acetate
DNA: desoxyribonucleic acid
PTSA: para-toluene sulfonic acid
RNA: ribonucleic acid
AZT: 3'-azido-2'-3'-dideoxy-thymidine or Zidovudine
BOP: benzotriazolyoxytrisdimethyl-aminophosphonium hexafluorophosphate
TLC: chromatography on thin-layer
DCC: N,N'-dicyclohexylcarbodiimide
DCU: N,N'-dicyclohexyluree
DIEA: N,N-diisopropyl N-ethylamine
DMZF: N,N-dimethylformamide
DHBV: duck hepatitis B virus
FAB$^+$: fast positiv atomic bombardment
$^3$HdTTP: thyroidinc triphosphate labelled with a radioactivity of 1 mCi/ml
HOBT: 1-hydroxybenzotriazole
IR: infra-red
MP: melting point
NMR: nuclear magnetic resonance
AIDS: acquired immuno deficiency syndrom
MS: mass spectrum
TBAF: tetrabutyldiphenylsilyle fluoride
TBDPSCl: tetrabutyldiphenylsilyle chloride
3-TC: (−)-(2R,3S)-2-hydroxymethyl-5-(cytosine-1'-yl)-1,3-oxathiolane or Lamivudine
TCIU: infection units
THF: tetrahydrofuran
RPM: round per minute
TsCl: tosyl chloride
UV: ultra-violet
HIV: human immunodeficiency virus
HBV: hepatitis B virus
HLTV: human lymphotropic T cells virus

TABLE I

Effect of the nucleosides of this invention on the inhibition of the replication of HIV I virus, expressed with the sum of $IC_{50}$

| Compounds n° | COMPOUNDS | $IC_{50}$ |
|---|---|---|
| 9 | | >100 µM |
| 10 | | 1–10 µM |
| 8 | | 10 µM |
| 6 | | |
| 7 | | |
| 2 | | 0.1–1 µM |
| 11 | | <100 µM |
| BCH-189 (reference product) | | 1 µM |

TABLE II

Effect of the nucleosides of this invention on the inhibition of the replication of DHBV virus

| Compounds n° | COMPOUNDS | $IC_{50}$ |
|---|---|---|
| BCH-189 (reference compound) | | 1 ± 0.5 µM |
| 2 | | 2 ± 0.5 µM |
| 8 | | 2 µM |
| 9 | | 2 µM |
| 10 | | 2 µM |
| 6 | | under testing |
| 7 | | under testing |

What is claimed is:

1. A 5-(cytosinyl-1) 1,3-oxathiolane of cis configuration (2R-5S) or (2S-5R) of the formula

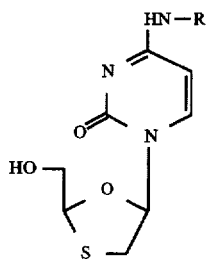

wherein R is an acyl group derived from a monocyclic or bicyclic nitrogenous heteroring or aralkyl derived from a monocyclic or bicyclic nitrogenous heteroring and its non-toxic, pharmaceutically acceptable acid addition salts.

2. A 5-(cytosinyl-1) 1,3-oxathiolane of claim 1 having a 2R-5S configuration.

3. A 5-(cytosinyl-1) 1,3-oxathiolane of claim 1 having a (2S-5R) configuration.

4. A compound of claim 1 wherein R is

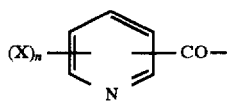

wherein X is selected from the group consisting of hydrogen, halogen, nitro, lower alkoxy and trifluoromethyl, n is an integer from 1 to 3 and —CO— is in position 2, 3 or 4.

5. A compound of claim 1 wherein R is

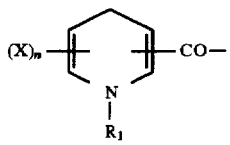

wherein $R_1$ is alkyl of 1 to 10 carbon atoms, X and n are defined as in claim 4 and —CO— is in position 2, 3 or 4.

6. A quaternized compound of claim 1 wherein R is

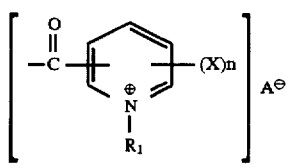

wherein $A^-$ is an inorganic anion, $R_1$ is alkyl of 1 to 10 carbon atoms, X and n are defined as in claim 4 and —CO— is in position 2, 3 or 4.

7. A compound of claim 1, wherein R is

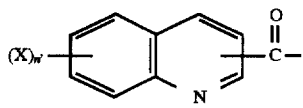

wherein —CO— is in position 2, 3 or 4, X is selected from the group consisting of hydrogen, halogen, trifluoromethyl, lower alkoxy and nitro and n' is an integer from 1 to 6.

8. A compound according to claim 1 wherein R is

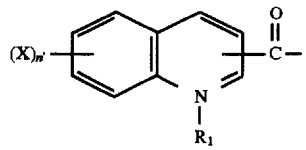

wherein $R_1$ is alkyl of 1 to 10 carbon atoms, X is selected from the group consisting of hydrogen, halogen, nitro, lower alkoxy, and trifluoromethyl and n' is an integer from 1 to 6.

9. A quaternized compound of claim 1 wherein R is

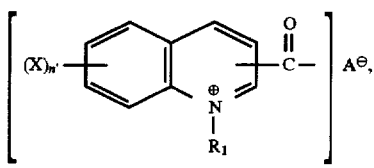

wherein $R_1$ is alkyl of 1 to 10 carbon atoms, X and n' are defined as in claim 4, the —CO— is present in position 2, 3 or 4 and A is an inorganic or organic anion.

10. A compound of claim 1 wherein R is

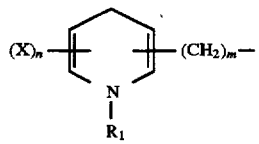

wherein $R_1$ is alkyl of 1 to 10 atoms, X and n are defined as in claim 4 and m is an integer from 1 to 6.

11. An optically-active isomer of a compound of claim 1.

12. A compound of claim 1 selected from the group consisting of 5-[$N^4$-(3" pyridyl carbonyl) cytosin-1'-yl]-1,3-oxathiolane and its non-toxic, pharmaceutically acceptable acid addition salts in racemic form or in optically-active form.

13. An anti-vital composition comprising an anti-virally effective amount of a compound of claim 1 and an inert, pharmaceutical carrier.

14. A method of combatting vital infections in warm-blooded animals comprising administering to warm-blooded animals an anti-virally effective amount of a compound of claim 1.

15. The method of claim 14 wherein the compound is selected from the group consisting of 5-[$N^4$-(3" pyridyl carbonyl) cytosin-1'-yl]-1,3-oxathiolane and its non-toxic, pharmaceutically acceptable acid addition salts in racemic form or in optically-active form.

* * * * *